United States Patent [19]

Hefner et al.

[11] Patent Number: 5,705,684
[45] Date of Patent: Jan. 6, 1998

[54] PREPARATION OF ACROLEIN, ACRYLIC ACID OR A MIXTURE THEREOF FROM PROPANE

[75] Inventors: Werner Hefner, Lampertheim; Otto Machhammer, Kirchheim; Hans-Peter Neumann, Ludwigshafen; Andreas Tenten, Maikammer; Wilhelm Ruppel, Frankenthal; Herbert Vogel, Ludwigshafen, all of Germany

[73] Assignee: BASF Aktiengesellschaft, Ludwigshafen, Germany

[21] Appl. No.: 618,440

[22] Filed: Mar. 8, 1996

[30] Foreign Application Priority Data

Mar. 10, 1995 [DE] Germany .......... 195 08 558.2
Jul. 13, 1995 [DE] Germany .......... 195 25 504.6

[51] Int. Cl.$^6$ .................................. C07C 51/16
[52] U.S. Cl. .................. 562/545; 562/546; 562/547; 568/476
[58] Field of Search .................. 562/545, 546, 562/547; 568/476

[56] References Cited

U.S. PATENT DOCUMENTS 3,865,873  2/1975  Oda et al. .............. 260/530
5,198,578  3/1993  Etzhorn et al. .......... 562/532
5,218,146  6/1993  Takata et al. ........... 562/535
5,262,547  11/1993 Ramachandran et al. .... 549/262
5,466,837  11/1995 Ramachandran et al. .... 549/55

FOREIGN PATENT DOCUMENTS 0 117 146  8/1984  European Pat. Off. .
2 118 939  11/1983 United Kingdom .

*Primary Examiner*—Joseph McKane
*Attorney, Agent, or Firm*—Oblon, Spivak, McClelland, Maier & Neustadt, P.C.

[57] ABSTRACT

In a process for preparing acrolein, acrylic acid or a mixture thereof from propane, propane is partially dehydrogenated to propylene in a first stage, the product gas mixture resulting therefrom is, after separating off hydrogen and water vapor, used as feed to an oxidation reactor, the propylene formed in the dehydrogenation is partially oxidized in the oxidation reactor using molecular oxygen in the presence of non-dehydrogenated propane as inert diluent gas to give acrolein, acrylic acid or a mixture thereof and the propane present in the product gas mixture of the partial oxidation is subsequently recirculated to the dehydrogenation stage A.

4 Claims, No Drawings

PREPARATION OF ACROLEIN, ACRYLIC ACID OR A MIXTURE THEREOF FROM PROPANE

The present invention relates to a process for preparing acrolein, acrylic acid or a mixture thereof from propane, in which A) in a first stage A, the propane is subjected to a partial heterogeneously catalyzed dehydrogenation in the gas phase to give propylene, B) the product gas mixture from stage A containing propylene and unreacted propane is used in a second stage B as feed to an oxidation reactor and in the oxidation reactor the propylene is subjected to a selective heterogeneously catalyzed gas-phase partial oxidation with molecular oxygen to give acrolein, acrylic acid or a mixture thereof as target product, with pure oxygen being used as oxygen source, and C) in a third stage C, the target product is separated from the product gas stream obtained from the partial oxidation of the propylene in stage B and at least the unreacted propane present in the product gas stream from stage B is recirculated to the dehydrogenation stage A.

Acrylic acid is an important chemical feedstock which is used, inter alia, as monomer for the preparation of polymers which, for example, are used in aqueous dispersion as binders. Acrolein is an important intermediate, for example in the preparation of glutaric dialdehyde, methionine, folic acid and acrylic acid.

It is generally known that acrylic acid can be prepared by heterogeneously catalyzed gas-phase oxidation of propylene using molecular oxygen over catalysts which are present in a solid aggregate state (cf., for example, DE-A 19 62 431, DE-A 29 43 707, DE-C 1 205 502, EP-A 257 565, EP-A 253 409, DE-B 22 51 364, EP-A 117 146, GB-B 1 450 986 and EP-A 293 224).

The catalysts used are normally oxide compositions. The catalytically active oxide composition can contain, apart from oxygen, only one other element or more than one other element (multi-element oxide compositions). The catalytically active oxide compositions used are particularly frequently those comprising more than one metallic, in particular transition metal, element. These are referred to as multimetal oxide compositions. The multielement oxide compositions are usually not simple physical mixtures of oxides of the elemental constituents, but heterogeneous mixtures of complex poly-compounds of these elements.

In general, the heterogeneously catalyzed gas-phase oxidation of propylene to acrylic acid is carried out at elevated temperature (normally a few hundred ° C, typically from 200 to 450° C).

Since the heterogeneously catalyzed gas-phase oxidation of propylene to acrylic acid is strongly exothermic, it is advantageously carried out in a fluidized bed or in multitube fixed-bed reactors where a heat exchange medium is passed through the space surrounding the contact tubes. The latter procedure is the preferred one (cf., for example, DE-A 44 31 957 and DE-A 44 31 949). The working pressure (absolute pressure) is normally from 1 to 10 bar. The target reaction occurs during the residence time of the reaction gas mixture in the catalyst charge through which it is passed.

As is generally known to those skilled in the art, the heterogeneously catalyzed gas-phase partial oxidation of propylene to acrylic acid proceeds essentially in two steps in succession along the reaction coordinate, of which the first leads to acrolein and the second from acrolein to acrylic acid. As a result, if the process of the invention is suitable for the preparation of acrylic acid from propylene by gas-phase catalytic oxidation, it is automatically also suitable for the preparation of acrolein from propylene by gas-phase catalytic oxidation, since the preparation of acrylic acid can at any time be stopped at the acrolein stage.

As a result of the pronounced exothermic character of the partial oxidation of propylene, the oxidation reactors are customarily fed with a gas mixture which contains the reactants molecular oxygen and propylene diluted with a gas which is essentially inert under the conditions of the gas-phase catalytic partial oxidation. Here, diluent gases are those whose constituents, considered individually, remain unaltered to an extent of more than 95 mol %, preferably more than 98 mol %, under the conditions of the heterogeneously catalyzed gas-phase partial oxidation. Usually, the inert diluent gas comprises the major proportion by volume of the three constituents of the feed gas mixture.

The classical methods of heterogeneously catalyzed gas-phase oxidation of propylene to acrolein and/or acrylic acid recommend steam and/or nitrogen as inert diluent gas (cf., for example, U.S. Pat. No. 4,147,885, column 1, lines 20 to 35, DE-A 20 56 614, page 2, last two lines, DE-B 20 09 172, column 4, lines 40 to 45, DE-A 22 02 734, p. 4, lines 18 to 22, DE-A 30 06 894, page 6, line 21 and DE-A 24 36 818, page 2, paragraph 3, with DE-A 20 56 614 attributing the particular suitability of steam as inert diluent gas to its relatively high molar heat capacity (page 4, paragraph 2, line 4), whereas DE-B 22 51 364 mentions the cost aspect of nitrogen as inert diluent gas (air as source of the oxidant) in respect of its frequent use).

A disadvantage of the classical processes for the heterogeneously catalyzed gas-phase oxidation of propylene to acrolein and/or acrylic acid is that, on the one hand, they require essentially pure propylene as propylene source, but propylene is a material which essentially does not occur naturally. Propylene is predominantly obtained as cracking gas in the cracking of petroleum hydrocarbons. In addition, the oxygen limit concentration of the feed gas comprising molecular oxygen, propylene and inert diluent gas in the classical processes is also unsatisfactory.

The oxygen limit concentration is that percentage by volume of molecular oxygen in the feed gas mixture below which, regardless of the proportions by volume of the other constituents of the feed gas mixture (in continuous operation, these proportions by volume can fluctuate unexpectedly as a result of faults), namely the organic compound to be partially oxidized (propylene) and the inert diluent gas, combustion of the organic substance initiated by a local ignition source, for example, local overheating or spark formation in the reactor, is no longer able to spread from the ignition source through the feed gas mixture at the given pressure and temperature, so as to exclude the danger of an explosion. This means that, for safety reasons, the proportion by volume of the molecular oxygen used as oxidant in the feed gas mixture has to lie below the oxygen limit concentration. Since on the other hand, with regard to the stoichiometry of the partial oxidation to the desired target compound, it is generally necessary to use the molecular oxygen employed as oxidant in at least stoichiometric or in superstoichiometric amounts (eg. to reoxidize the oxidic composition used as catalyst and to reduce carbon deposits), the oxygen limit concentration of the feed gas mixture influences the maximum proportion by volume of the organic compound to be partially oxidized (propylene) in the feed gas mixture and thus the achievable space-time yield of target product (cf. also EP-A 257 565, page 5, lines 36/37).

Since those skilled in the art generally look for a space-time yield of the desired target compound which is as high as possible, there is interest in making the proportion by volume of the reactants in the feed gas mixture as high as possible, ie. to select the inert diluent gas so that it gives an oxygen limit concentration which is as high as possible.

British Patent No. 1 450 986 recommends, particularly because of its relatively high ability to absorb heat, the use of carbon dioxide as essentially the only inert diluent gas for avoiding the danger of explosion in the gas-phase catalytic oxidation for preparing acrylic acid from propylene.

DE-A 19 24 431 likewise concerns a gas-phase catalytic oxidation process for preparing acrylic acid from propylene. As suitable inert diluent gases, DE-A 19 62 431 mentions nitrogen, steam, carbon dioxide or saturated hydrocarbons.

DE-B 22 51 364 recommends, for the heterogeneously catalyzed gas-phase process for the partial oxidation of propylene to acrylic acid, steam as inert diluent gas, to which nitrogen or saturated hydrocarbons such as methane, propane or butane can be added. DE-A 14 68 429 recommends carbon dioxide, nitrogen, saturated hydrocarbons or steam as inert diluent gases in a process for the heterogeneously catalyzed gas-phase oxidation of propylene to acrylic acid, with preference being given to steam.

However, all the examples of DE-A 19 62 431, DE-B 22 51 364 and DE-A 14 68 429 do not include any example in which a saturated hydrocarbon would even have been used as part of the inert diluent gas.

DE-A 30 06 894 likewise concerns, in a heterogeneously catalyzed gas-phase partial oxidation process for propylene, the problems of, on the one hand, preventing a runaway reaction and, on the other hand, achieving a productivity which is as high as possible (p. 2, lines 11 to 19). The solution recommended is to feed in the feed gas mixture at low catalyst activity and subsequently to successively increase the catalyst activity along the reaction coordinate. Possible inert diluent gases mentioned in DE-A 30 06 894 are nitrogen, carbon dioxide and/or steam.

German Auslegeschrift 17 93 302 relates to a process of heterogeneously catalyzed gas-phase partial oxidation in which the inert diluent gas used is, after separating off the target product, the reaction off-gas containing the carbon oxides and water vapor produced in the reaction. DE-A 20 56 614 likewise speaks of the problems of preventing explosion-like combustion processes in the heterogeneously catalyzed gas-phase partial oxidation of propylene (eg. p. 3, paragraph 2, last two lines). To avoid disadvantageous effects of the preferred diluent gas steam, DE-A 20 56 614 recommends recirculating the reaction off-gases substantially freed of condensible gases, with partial or complete replacement of the water vapor, to the oxidation reactor as inert diluent gases and at the same time feeding the feed gas mixture in at low catalyst activity and subsequently increasing the catalyst activity successively along the reaction coordinate. Since the oxidant "molecular oxygen" is fed in as a constituent of air, the effective inert diluent gases in the method of DE-A 20 56 614 are essentially nitrogen and carbon dioxide. The method of DE-A 24 36 818 corresponds, in terms of the inert diluent gases used, essentially to that of DE-A 20 56 614. The same applies to U.S. Pat. No. 4,147,885. DE-A 27 29 841 relates to a process for the heterogeneously catalyzed gas-phase oxidation of propylene to acrylic acid, which, owing to the use of a specific oxidation catalyst, makes it possible to use, in place of steam as inert diluent, a mixture of CO, $CO_2$, nitrogen and argon which is separated from the product gas mixture of the heterogeneously catalyzed partial oxidation and is recirculated to the feed gas mixture.

EP-B 253 409 (cf., in particular, p. 5, first three lines) and EP-A 257 565 teach, for avoiding an explosion risk in the heterogeneously catalyzed gas-phase partial oxidation of propylene, the use of those inert diluent gases which have an increased molar heat capacity Cp. Preference is here given, for example on page 4, lines 47 ff of EP-B 253 409 and on p. 5, lines 26 ff of EP-A 257 565, to mixtures of nitrogen, $CO_2$, methane, ethane, propane and steam. However, apart from the gases specified, it is also possible for helium, argon, other saturated hydrocarbon gases, $N_2O$ and carbon monoxide to be additionally present. Only its mean molar heat capacity is considered important for the action of the inert diluent gas. Thus, the inert diluent gas of the feed gas mixture in all examples comprises more than 55% by volume of $N_2$. EP-B 253 409 (page 5, line 41) and EP-A 257 565 (page 6, line 26) recommend as particularly preferable those inert diluent gas mixtures whose specific molar heat $C_p$ is from 10 to 17 cal/mol.K under the operating conditions. Essentially pure propane, having a corresponding $C_p$ of 29.75 cal/mol.K, lies far outside this recommendation.

EP-A 293 224 concerns a process for the heterogeneously catalyzed gas-phase oxidation of propylene to acrylic acid, in which the use of a gas mixture containing carbon dioxide, steam and saturated hydrocarbons having from 1 to 5 carbon atoms is recommended as inert gas to ensure that the process can be carried out safely (p. 3, lines 9 and 20 of EP-A 293 224). EP-A 293 224 considers the presence of carbon oxides in relatively high concentrations (page 3, line 57) and a relatively high molar heat capacity of the inert gas mixture (page 3, line 57) to be essential to the effectiveness of the inert gas mixture recommended in EP-A 293 224. EP-A 293 224 considers a further particular advantage of the procedure it recommends to be the fact that a considerable part of the inert gas mixture to be used can be obtained from the product gas mixture of the partial oxidation. In all examples, the inert gas mixture used in the feed gas mixture comprises steam and $CO_2$ in a total amount of at least 15% by volume, based on the inert gas mixture.

Disadvantages of the abovementioned processes of the prior art for the heterogeneously catalyzed gas-phase oxidation of propylene to acrylic acid are that the associated oxygen limit concentrations are not satisfactory and the processes start from essentially pure propylene as the propylene source. The first also applies to the method of EP-A 117 146. EP-A 117 146 concerns a process for reacting propane which occurs in natural gas to give acrylic acid. In this method, the propane is subjected in a first process stage to a heterogeneously catalyzed partial dehydrogenation in the gas phase to give propylene. The propylene thus formed is subsequently subjected to the heterogeneously catalyzed gas-phase partial oxidation to give acrylic acid. Since the heterogeneously catalyzed dehydrogenation of propane to propylene is, for reasons of selectivity, customarily carried out at propane conversions lying significantly below 100%, little importance is normally attached to this variant for preparing propylene because the very similar boiling behavior of propylene formed and unreacted propane makes separation of these components complicated. In addition, removal of byproducts, eg. hydrogen, is necessary. The inventive feature of EP-A 117 146 is therefore the discovery that the main constituents apart from propylene in the product gas mixture of the propane dehydrogenation are essentially inert in respect of the subsequent heterogeneously catalyzed gas-phase partial oxidation of the propylene, so that the product gas mixture from the propane dehydrogenation can be transferred completely without significant disadvantages to the subsequent propylene oxidation stage and the inert constituents can subsequently be recirculated to the propane dehydrogenation stage. EP-B 253 409 and EP-A 257 565 gave those skilled in the art no cause for deviating from this method of EP-A 117 146, even though the mean molar specific heat of an inert gas mixture consisting of propane and hydrogen lies just within the range recommended as preferred by EP-A 117 146 and EP-B 253 409. The above-mentioned documents suggest at most that water vapor used and/or formed in the propane dehydrogenation be frozen out before the dehydrogenation product gas mixture is passed on. However, as already mentioned, the disadvantage of the procedure recommended by EP-A 117 146 is that the oxygen limit concentration of the feed gas mixture of the propylene oxidation stage is not satisfactory even in the context of this procedure.

It is an object of the present invention to provide a process for preparing acrolein, acrylic acid or a mixture thereof which does not have the disadvantages of the processes of the prior art.

We have found that this object is achieved by a process for preparing acrolein, acrylic acid or a mixture thereof from propane, in which A) in a first stage A, the propane is subjected to a partial heterogeneously catalyzed dehydrogenation in the gas phase to give propylene, B) the product gas mixture from stage A containing propylene and unreacted propane is used in a second stage B as feed to an oxidation reactor and in the oxidation reactor the propylene is subjected to a selective heterogeneously catalyzed gas-phase partial oxidation with molecular oxygen to give acrolein, acrylic acid or a mixture thereof as target product, with pure oxygen being used as oxygen source, and C) in a third stage C, the target product is separated from the product gas stream obtained from the partial oxidation of the propylene in stage B and at least the unreacted propane present in the product gas stream from stage B is recirculated to the dehydrogenation stage A, wherein, from among the constituents other than propane and propylene present in the product gas mixture from stage A, at least the hydrogen and the water vapor are separated from the product gas mixture before it is used as feed to the oxidation reactor of the second stage B.

This means that, after addition of molecular oxygen, the oxidation stage B is fed with a feed gas mixture consisting essentially of only propylene, molecular oxygen and propane. The latter constituent is essentially the inert diluent gas, while the first two constituents are the reactants. There are two reasons for this feed gas mixture being advantageous. Firstly, it can be obtained in a simple manner starting from the naturally occurring raw material propane (hydrogen and water vapor can be removed in a simple manner known per se, while the complicated propane/propylene separation can be omitted), and on the other hand the mixture oxygen/propylene/propane has an increased oxygen limit concentration. The latter fact is the result of comprehensive and systematic research work. It is based on the recognition that the oxygen limit concentration of a feed gas mixture comprising molecular oxygen, inert diluent gas and propylene (the proportion of molecular oxygen decreases along the reaction coordinate) is influenced less by the molar heat capacity $C_p$ of the inert diluent gas than by the inert diluent gas itself being an essentially combustible, lower organic compound, with the simultaneous requirement of inertness necessitating the restriction to lower saturated hydrocarbons. Among the latter, propane is advantageous insofar as if it is not completely inert in the oxidation stage, it is itself essentially converted to propylene, acrolein and/or acrylic acid.

The feature "combustible" here indicates compounds whose mixtures with air at an initial pressure of 1 bar and an initial temperature of 50° to 150° C. have an upper and a lower explosive limit (ignition limit), with the determination of the explosive limits being based on measurement in the standard apparatus as described by W. Berthold et al. in Chem.-Ing. Tech. 56 (1984) No. 2, pp. 126-127.

In this context, explosive limits are the following limit values in accordance with DIN 51649:

In a mixture of air and a combustible gas, the velocity at which, under prescribed initial conditions, combustion (ignition, explosion) initiated by a local ignition source (eg. glowing platinum wire) spreads is dependent on the combustible gas content. It is greatest at a particular content. Either decreasing or increasing the combustible gas content reduces the combustion velocity until finally, at a lower and an upper limit value for the combustible gas content, the combustion reaction just no longer spreads out from the ignition source. These two limit values are the lower explosive limit and the upper explosive limit, the range of combustible gas content lying between them is the explosive region (ignition region).

The higher the proportion of propane in the inert diluent gas of the feed gas mixture for the heterogeneously catalyzed gas-phase oxidation of propylene, the more safely this reaction can be carried out even with increased proportions by volume of the reactants.

To achieve useful conversions in the propane dehydrogenation, the reaction has to be carried out at relatively high temperatures (typically from 300° to 700° C.). Since the dehydrogenation (cleavage of C—H) has a thermodynamic disadvantage compared with cracking (cleavage of C—C), it is carried out over selective catalysts. One hydrogen molecule is produced as byproduct for each propylene molecule formed. As a result of the selective catalysts, methane and ethane are formed as further byproducts in only subordinate amounts. Since the dehydrogenation reaction proceeds with an increase in volume, the conversion can be increased by lowering the partial pressure of the reactants. This can be achieved in a simple manner, eg. by mixing in steam which constitutes an inert gas for the actual dehydrogenation reaction. Dilution with steam gives the further advantage of reduced carbonization of the catalyst used, since the steam reacts with the carbon by the water gas reaction. In addition, steam can be easily separated from the product gas mixture of the dehydrogenation, eg. by condensation. A further way of increasing the conversion in the dehydrogenation is by taking hydrogen out of the equilibrium by chemical means. The simplest method is the addition of oxygen to the reaction mixture. This is then referred to as oxidative dehydrogenation in which water vapor is formed as byproduct as a result of the reaction of the oxygen with hydrogen. The detailed relationships are known to those skilled in the art and are described, including the dehydrogenation catalysts to be used, in, for example: EP-A 117 146, U.S. Pat. No. 3,784,483, U.S. Pat. No. 4,083,883, U.S. Pat. No. 3,692,701, U.S. Pat. No. 4,005,985, U.S. Pat. No. 4,041,099, U.S. Pat. No. 4,144,277 and U.S. Pat. No. 4,176,410. The product gas mixtures obtained can therefore be ones whose main constituents are unreacted propane, possibly unreacted oxygen, propylene formed as target product, hydrogen formed as byproduct and possibly water vapor. Methane, ethane, CO and $CO_2$ are present in subordinate amounts at most.

This means that removal of hydrogen and water vapor present in the dehydrogenation product gas mixture (eg. by fractional condensation) gives a gas mixture which consists essentially of only propylene, propane and possibly small amounts of $O_2$ and can be used for the purposes of the process of the invention as feed to the oxidation reactor of stage B. The amount of the molecular $O_2$ acting as oxidant which is to be mixed into the feed gas mixture is matched to the propylene amount present therein. The propylene/propane ratio is assessed in a manner known to those skilled in the art via the conversion in the dehydrogenation. As a result of the above-described procedure, the feed gas mixture for the oxidation reactor of stage B in the process of the invention should contain, based on propane present therein, not more than 5% by volume of constituents other than propane, propylene, ethane, methane and molecular oxygen. In a preferred embodiment of the process of the invention, all constituents other than propane, propylene and, if desired, molecular oxygen are removed from the product gas mixture of stage A of the process of the invention. The separation methods to be used for this purpose, such as fractional condensation or absorption and extraction processes, are known to those skilled in the art and require no further explanation. For example, $CO_2$ can be removed by scrubbing the gas mixture with an aqueous, basic solution. Since molecular oxygen occurs in air only in association with $N_2$, the molecular oxygen required as oxidant in the oxidation stage B of the process of the invention is to be taken, according to the invention, from an essentially pure oxygen source.

As already mentioned, the heterogeneously catalyzed gas-phase partial oxidation of propylene to acrylic acid with molecular oxygen proceeds in principle in two successive steps along the reaction coordinate, of which the first leads to acrolein and the second leads from acrolein to acrylic acid. The reaction proceeding in two temporally successive steps makes it possible, in a manner known per se, to configure the stage B of the process of the invention as two oxidation stages arranged in succession, with the oxidic catalyst used in each of the oxidation stages being able to be optimized for the respective oxidation stage. Thus, for the first oxidation stage (propylene→acrolein), preference is generally given to a catalyst based on multimetal oxides containing the element combination Mo—Bi—Fe, while for the second oxidation stage (acrolein→acrylic acid) preference is normally given to catalysts based on multimetal oxides containing the element combination Mo—V. Appropriate multimetal oxide catalysts for the two oxidation stages have been described many times and are well known to those skilled in the art. For example, page 5 of EP-A 253 409 refers to appropriate U.S. patents. Useful catalysts for the two oxidation stages are also disclosed in DE-A 44 31 957 and DE-A 44 31 949: this applies in particular to those of the general formula I in the two documents. The product mixture of the first oxidation stage is generally transferred without intermediate treatment to the second oxidation stage. The simplest embodiment of the two oxidation stages is therefore formed by a tube-bundle reactor within which the catalyst charge alters appropriately along the individual contact tubes with completion of the first reaction step. However, the two oxidation stages are preferably carried out in an oxidation reactor comprising two oxidation reactors in series. In this case, the other reaction conditions, eg. the reaction temperature, can also be optimized in a simple manner for the respective oxidation stage. The molecular oxygen required for the second oxidation stage is here advantageously only fed into the feed gas mixture for the second oxidation reactor. Preferably, for both oxidation stages, the volume ratio of organic compound to be partially oxidized (propylene or acrolein): molecular oxygen in the feed gas mixture is selected as 1:1 to 3, preferably 1:1.5 to 2 (this also applies to a stage B which ends at acrolein). As already mentioned, the excess of oxygen in both oxidation stages has an advantageous effect on the kinetics of the gas-phase oxidation. The thermodynamic conditions are not significantly influenced thereby, since the heterogeneously catalyzed gas-phase partial oxidation of the propylene to acrylic acid is subject to kinetic control. In principle, the heterogeneously catalyzed gas-phase partial oxidation of propylene to acrylic acid can also, however, be carried out in a single stage. In this case, both reaction steps occur in one oxidation reactor which is charged with a catalyst which catalyzes both reaction steps. Of course, the catalyst charge can also change continuously or abruptly along the reaction coordinate within one oxidation stage. Naturally, in an embodiment of the stage B of the invention in the form of two oxidation reactors connected in series, carbon oxide and water vapor formed as byproducts in the first oxidation reactor can be separated if necessary from the product gas stream leaving the first oxidation reactor before it is passed on to the second oxidation reactor.

Otherwise, the reaction temperatures and pressures to be cited in the stage B are known to those skilled in the art from the literature.

The product gas mixture leaving the stage B is composed essentially of the target product acrolein, acrylic acid or a mixture thereof, unreacted propylene, unreacted acrolein, unreacted molecular oxygen, water vapor formed as byproduct, carbon oxides formed as byproduct, the inert diluent gas propane and small amounts of other lower aldehydes and hydrocarbons.

The target product is separated from the product gas mixture in a manner known per se (eg. absorption of acrylic acid in water or in a high-boiling hydrophobic organic solvent or absorption of acrolein in water or in aqueous solutions of lower carboxylic acids and subsequent work-up of the absorbate; cf., for example, EP-A 117 146 and DE-A 43 08 087 or DE-A 43 35 172 and also DE-A 44 36 243). Unreacted propylene and/or acrolein are, if desired, likewise separated off and recirculated to the stage B. Otherwise, the significant constituents other than acrylic acid and acrolein can, as necessary and depending on the dehydrogenation catalyst used, each be separated off separately or recirculated together with the propane to the dehydrogenation stage A, so as to, as described, influence the dehydrogenation conversion. Of course, propane on its own can also be recirculated to the stage A. If the process of the invention is carried out continuously, there thus results a continuous conversion of propane to acrylic acid and/or acrolein.

In summary, the differences between the process of the invention and the processes of the prior art are essentially that, firstly, propane can be used as starting material and, when using otherwise identical reaction conditions, the heterogeneously catalyzed gas-phase oxidation of propylene to acrolein, acrylic acid or a mixture thereof, particularly at increased proportions by volume of reactants in the feed gas mixture of the gas phase oxidation, can be carried out with increased safety owing to the function of unreacted propane as essentially the sole inert diluent gas (even the feed of molecular oxygen can fluctuate in continuous operation owing to unexpected faults) which forms the basis for increased space-time yields of target product. This is demonstrated below by some examples. It may be affirmed that, according to the process method of the invention, it is possible to handle more safely feed gas mixtures of the stage B whose propylene feed is from >30% by volume up to 40 to 45% by volume, based on the feed gas mixture.

Useful feed gas mixtures of the stage B comprise
from 15 to 30% by volume of propylene
from 20 to 40% by volume of oxygen and
from 30 to 65% by volume of propane.

They can be obtained in a simple manner by selecting the conversion in the stage A as from 25 to 35 mol % and, after separating off hydrogen, water vapor and, if appropriate, other byproducts, adding the appropriate amount of molecular oxygen.

The process of the invention can be used particularly advantageously if the raw material used for the preparation by gas-phase catalytic oxidation of acrolein and/or acrylic acid is refinery polypropylene. This comprises about 70% by volume of propylene and about 30% by volume of propane.

The refinery propylene is advantageously first used as feed to an oxidation reactor and in the oxidation reactor the propylene is, in accordance with stage B of the process of the invention, subjected to a selective heterogeneously catalyzed gas-phase partial oxidation to give acrolein, acrylic acid or a mixture thereof as target product and, in a stage C) of the invention, the target product is separated from the product stream obtained from the partial oxidation of the propylene in the stage B and at least the unreacted propane present in the product gas stream of the stage B is recirculated to a dehydrogenation stage A of the invention, so as to subsequently proceed further in accordance with the invention.

EXAMPLES (influence of the combustibility of the inert diluent gas constituents on the oxygen limit concentration)

Determination of the oxygen limit concentration of feed gas mixtures at an initial temperature of 250° C. and an initial pressure of 1 bar and comprising propylene (organic compound to be partially oxidized), molecular oxygen (oxidant) and an inert diluent gas which is inert in respect of a heterogeneously catalyzed gas-phase partial oxidation of the propylene to acrylic acid.

General experimental procedure:

The experiments were carried out in a closed, spherical 5 l high-pressure vessel of stainless steel. The formation of the gas mixture in the initially evacuated high-pressure vessel was carried out by the partial pressure method. After mixing for 10 minutes by means of a magnetic stirrer, an attempt was made to ignite the gas mixture by means of a melting platinum wire. Any independent spreading of a reaction front (explosion) triggered thereby was detected by the rise with time of the internal pressure of the vessel (measured using a piezoelectric transducer) and by the increase in temperature in the vessel.

Results (the specific molar heats $C_p$ used are based on the data from "Ihsan Barin, Thermochemical Data of Pure Substances, Part I and Part II, VCH Verlgasgesellschaft, Weinheim, Second Edition, 1993", with ideal gas behavior being assumed for the gas mixtures):

a) Exclusive use of methane as inert combustible diluent gas, ie. the inert diluent gas consisted entirely of combustible constituents. The specific molar heat $C_p$ of methane is 47.5 J/mol.K under the specified conditions. The oxygen limit concentration determined is 32% by volume.

This means that, in a mixture of propylene, molecular $O_2$ and methane as inert gas, which is at 250° C. and 1 bar, a local ignition (explosion) can, regardless of the specific composition of the mixture, no longer spread independently when the proportion by volume of $O_2$ in the total mixture is <32% by volume, ie. in a mixture of 31% by volume of $O_2$, 20% by volume of propylene and 49% by volume of methane at 1 bar and 250° C., a local ignition can no longer spread independently.

b) Use of a 3.2 (propane): 96.8 ($CO_2$) mixture (ratio of the proportions by volume) of propane and carbon dioxide as inert diluent gas, ie. the inert diluent gas consisted virtually entirely of non-combustible diluent gas. The composition of the inert gas mixture was selected in such a way that it likewise had a $C_p$ of 47.5 J/mol.K under the specified conditions. The oxygen limit concentration determined is only 15% by volume.

This means that in a mixture of 31% by volume of $O_2$, 20% by volume of propylene and 49% by volume of the inert diluent gas under conditions corresponding to a), a local ignition spreads independently.

c) Use of a 48.3 (propane): 51.7 (methane) mixture (ratio of the proportions by volume) of propane and methane as inert diluent gas, ie. the inert diluent gas consisted entirely of combustible constituents. The specific molar heat $C_p$ of this mixture is 80.8 J/mol.K under the specified conditions. The oxygen limit concentration determined is 37% by volume.

d) Use of a 50 (propane): 50 ($CO_2$) mixture (ratio of the proportions by volume) of propane and carbon dioxide as inert diluent gas, ie. the inert diluent gas also contained non-combustible constituents. The composition of the inert gas mixture was selected in such a way that it likewise has a $C_p$ of 80.8 J/mol.K under the specified conditions.

The oxygen limit concentration determined is only 34% by volume, ie. despite a significantly higher $C_p$ value for the inert diluent gas in comparison with a), the oxygen limit concentration is only a proportion by volume comparable with a).

We claim:

1. A process for preparing acrolein, acrylic acid or a mixture thereof from propane, in which A) in a first stage A, the propane is subjected to a partial heterogeneously catalyzed dehydrogenation in the gas phase to give propylene, B) the product gas mixture from stage A containing propylene and unreacted propane is used in a second stage B as feed to an oxidation reactor and in the oxidation reactor the propylene is subjected to a selective heterogeneously catalyzed gas-phase partial oxidation with molecular oxygen to give acrolein, acrylic acid or a mixture thereof as target product, with pure oxygen being used as oxygen source, and C) in a third stage C, the target product is separated from the product gas stream obtained from the partial oxidation of the propylene in stage B and at least the unreacted propane present in the product gas stream from stage B is recirculated to the dehydrogenation stage A, wherein, from among the constituents other than propane and propylene present in the product gas mixture from stage A, at least the hydrogen and the water vapor are separated from the product gas mixture before it is used as feed to the oxidation reactor of the second stage B.

2. A process as claimed in claim 1, wherein the total amount of constituents other than propane and propylene present in the product gas mixture of stage A are removed therefrom before it is used as feed to the oxidation reactor of the second stage B.

3. A process as claimed in claim 1, wherein the stage B is implemented in the form of two oxidation reactors connected in series, of which the first is charged with a multimetal oxide catalyst containing the element combination Mo—Bi—Fe and the second is charged with a multimetal oxide catalyst containing the element combination Mo—V.

4. A process as claimed in claim 3, wherein the product gas mixture of the first oxidation reactor is transferred without intermediate treatment to the second oxidation reactor, with the volume ratio of organic compound to be partially oxidized (propylene or acrolein):molecular oxygen being set at 1:1 to 3 in the feed gas mixtures of both oxidation reactors.

* * * * *